(12) United States Patent
Peilstöcker et al.

(10) Patent No.: US 7,358,397 B2
(45) Date of Patent: Apr. 15, 2008

(54) PREPARATION OF HALOGENATED 4-AMINOPHENOLS

(75) Inventors: Karen Peilstöcker, Köln (DE); Albrecht Marhold, Leverkusen (DE); Jens-Peter Joschek, Köln (DE)

(73) Assignee: LANXESS Deutschland GmbH, Leverkusen (DE)

( * ) Notice: Subject to any disclaimer, the term of this patent is extended or adjusted under 35 U.S.C. 154(b) by 373 days.

(21) Appl. No.: 10/934,919

(22) Filed: Sep. 3, 2004

(65) Prior Publication Data
US 2005/0143425 A1 Jun. 30, 2005

(30) Foreign Application Priority Data
Sep. 9, 2003 (DE) ................ 103 41 533

(51) Int. Cl.
C07C 257/14 (2006.01)
C07D 213/62 (2006.01)

(52) U.S. Cl. ........................ 564/247; 546/261

(58) Field of Classification Search ............... None
See application file for complete search history.

(56) References Cited

U.S. PATENT DOCUMENTS

| | | | |
|---|---|---|---|
| 4,939,170 A | 7/1990 | Krüger et al. | 514/483 |
| 5,132,325 A | 7/1992 | Drabek | 514/594 |
| 5,176,914 A | 1/1993 | Krüger et al. | 424/405 |
| 6,124,504 A | 9/2000 | Hupperts et al. | 564/415 |

FOREIGN PATENT DOCUMENTS

| | | |
|---|---|---|
| CH | 452 270 | 5/1968 |
| DE | 38 27 133 A1 | 8/1987 |
| DE | 41 19 919 A1 | 6/1990 |
| JP | 61 126055 | 6/1986 |
| JP | 63-310850 | 12/1988 |
| JP | 5 125030 | 5/1993 |
| WO | 03/002154 | 1/2003 |
| WO | 03/008413 | 1/2003 |
| WO | 03/076405 | 1/2003 |

OTHER PUBLICATIONS

Database CAPLUS on STN, Acc, No. 1941:24736, Brode et al., Journal of Organic Chemistry (1941), 6, p. 341-348 (abstract).*
Nam S. et al.: "Non-enzymatic reduction of azo dyes by NADH" Chemosphere, Bd. 40, Nr. 4, Feb. 2000, Seiten 351-357, XP002307653 GB Pergamon Press, Oxford. Seite 352, Absatz 2.2; Seiten 354, 355, Absatz 3.2.
Database CA 'Online! Chemical Abstracts Service, Columbus, Ohio, US; Chlost, Milan et al; "Substituted 4-aminophenols" XP002307658 gefunden im STN Database accession No. 1980:94048 Zusammenfassung & CS 178 694 B (CZECH.) May 15, 1979.
Birchall, J. M. et al.: "Polyfluoroarenes. Part X. Polyfluoroaromatic azo-compounds", Journal of the Chemical Society, Section C: Organic Chemistry., Nr. 3, 1970, Seiten 449-455, XP002307654 GB Chemical Society. Letchworth. Seite 454, linker Spalte "nonafluoro-4-hydroxyazobenzene"; Seite 455, Absatz (f).
Hunter, L. et al.: "CCLXVII.—Halogen derivatives of o- and p-azophenol", Journal of the Chemical Society., 1928, Seiten 2051-2058, XP008039233 GB Chemical Society. Letchworth. Seite 2054-Seite 2055.
Barnard, S. et al: "The effect of fluorine substitution on the physicochemical properties and the analgesic activity of paracetamol", Journal of Pharmacy and Pharmacology, 45(8), 736-44, CODEN: JPPMAB; ISSN: 0022-3573, 1993, XP008039145 Verbindungen der Formel 9, 13 and 19.
Sander W. et al.: "4-Oxo-2,3,5,6-tetrafluorocyclohexa-2,5-dienylidene—A highly electrophilic triplet carbene", Chemistry—A European Journal, Bd. 6, Nr. 34, 2000, Seiten 4567-4579, XP002307655 USVCH Publishers. Seite 4578, linker Spalte, zweite Absatz.
Meldola R. et al.: "CXXXIX.—Quinone-ammonium derivatives. Part III. dihaloid-, monoazo-, bisazo-, nitrotriazo-, and bistriazo-compounds: attempts to prepare derivatives containing an asymmetric quinquevalent nitrogen atom" Journal of the Chemical Society., Nr. 105, 1914, Seiten 1469-1487, XP008039238 GB Chemical Society. Letchworth. Seiten 1472 und 1473, Formeln I, II.
Kohn M. et al.: "Chlorierung des p-Amidophenols (XXXV. Mitteilung über Bromphenole)", Monatshefte Fur Chemie., Bd. 56, 1930, Seiten 137-142, XP008039205 at Springer Verlag. Wien. Seite 137, Verbindungen der Formel I und II.
Shimao I. et al.: "Reaction of haloazoxybenzenes with sulfuric acid", Bulletin of the Chemical Society of Japan., Bd. 55, Nr. 2, 1982, Seiten 546-550, XP002307656 JP Japan Publications Trading Co. Tokyo. Verbindungen 4b und 4c in Seiten 546 und 550.
Allen D. W. et al.: "Solvatochromic and halochromic properties of some phosphonioarylimino-and phosphonioarylazo-phenolate betaine dyes" Journal of the Chemical Society, Perkin Transactions 2., Nr. 6, 1997, Seiten 1099-1103, XP002307657 GB Chemical Society. Letchworth. Seite 1102, linker Spalte: "Synthesis of o-bromophenylazophenols".

* cited by examiner

Primary Examiner—Brian Davis
(74) Attorney, Agent, or Firm—Michael A. Miller

(57) ABSTRACT

The present invention relates to halogenated 4-aminophenols and to halogenated 4-(phenyidiazenyl)phenols, to a process for their preparation and to the use of the halogenated 4-hydroxyphenols for preparing active ingredients, especially in pharmaceuticals and agrochemicals.

3 Claims, No Drawings

PREPARATION OF HALOGENATED 4-AMINOPHENOLS

BACKGROUND

The present invention relates to halogenated 4-aminophenols and to halogenated 4-(phenyldiazenyl)phenols, to a process for their preparation and to the use of the halogenated 4-hydroxyphenols for preparing active ingredients, especially in pharmaceuticals and agrochemicals.

Halogenated phenols, especially fluorinated phenols, are valuable starting materials for the preparation of active ingredients inpharmaceuticals and agrochemicals, since the fluorine substituents increase the lipophilicity and therefore the membrane permeability of the entire active ingredient molecule. For example, fluorinated 4-hydroxyanilines are particularly suitable as starting materials for preparing active ingredients which are used for treating chronic bronchitis (see also WO 03/08413 and PCT/03/02154).

The preparation, for example, of 2,5-difluoro-4-hydroxyaniline is typically effected by nitrating 2,5-difluorophenol and subsequently reducing (see JP-A 63 310850).

A disadvantage of this synthetic route is that the nitration reaction does not proceed selectively and the 4-nitrophenol desired as an intermediate is obtainable only in poor yields.

There is therefore a need to provide a process which enables the preparation of halogenated 4-aminophenols in good yields and in a simple manner.

SUMMARY

The invention relates to a process for preparing a compound of the formula (I):

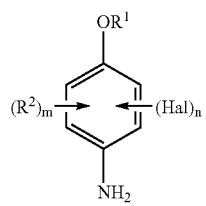

wherein
m is 0, 1, 2 or 3 and
n is 1, 2, 3 or 4,
where the sum of
m+n is a maximum of 4, and
$R^1$ is hydrogen, $C_1$-$C_{12}$-alkyl or $C_5$-$C_{15}$-arylalkyl and
$R^2$ is in each case independently $C_1$-$C_{12}$-fluoroalkyl, $C_1$-$C_{12}$-fluoroalkylthio or $C_1$-$C_{12}$-fluoroalkoxy and
Hal is in each case independently bromine, chlorine or fluorine.

The process involves the steps of A1, converting compounds of the formula (II)

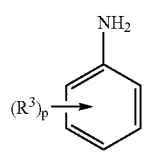

in which
p is 0, 1, 2 or 3 and
$R^3$ is in each case independently fluorine, chlorine, bromine, iodine, cyano, thiocyanato, hydroxysulphonyl or alkali metal salts thereof, nitro, $C_1$-$C_{12}$-alkyl, $C_1$-$C_{12}$-fluoroalkyl, $C_1$-$C_{12}$-fluoroalkyoxy, $C_1$-$C_{12}$-fluoroalkylthio, $C_1$-$C_{12}$-alkoxy, $C_1$-$C_{12}$-alkoxycarbonyl, di($C_1$-$C_{12}$-alkyl)amino, $C_4$-$C_{14}$-aryl or $C_5$-$C_{15}$-arylalkyl
to diazonium salts of the formula (III)

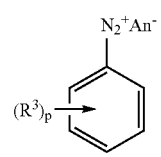

in which $An^-$ is the anion of an acid and
A2) reacting
the diazonium salts of the formula (III) with compounds of the formula (IV)

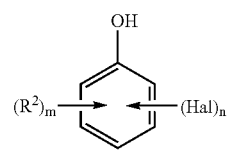

in which
m, n, Hal and $R^2$ are each as defined under the formula (I) in the presence of a base to give compounds of the formula (V)

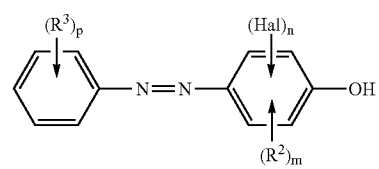

and
B) converting the compounds of the formula (V) with a reducing agent to a compound of the formula (I) that has $R^1$ is hydrogen, thereby forming at least one compound of formula (I).

In one embodiment, the invention relates to a compound of the formula (I):

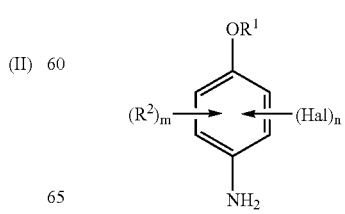

wherein
m is 0, 1, 2 or 3 and
n is 1, 2, 3 or 4,
m+n is a maximum of 4, and
$R^1$ is hydrogen, $C^1$-$C_{12}$-alkyl or $C_5$-$C_{15}$-arylalkyl and
$R^2$ is in each case independently $C_1$-$C_{12}$-fluoroalkyl, $C_1$-$C_{12}$-fluoroalkylthio or $C_1$-$C_{12}$-fluoroalkoxy and
Hal is in each case independently bromine, chlorine or fluorine,
wherein the compound of formula (I) excludes a compound selected from the group consisting of 4-amino-3,5-difluorophenol, 4-amino-2,5-difluorophenol, 4-amino-2,6-difluorophenol, 4-amino-2-chloro-6-fluorophenol, 4-amino-2-chloro-3-fluorophenol, 4-amino-2-chloro-5-fluorophenol, 4-amino-2-bromo-5-fluorophenol, 4-amino-2-fluorophenol, 4-amino-3-fluorophenol, 4-amino-2-(trifluoromethyl)phenol, 4-amino-5-chloro-2-(trifluoromethyl)phenol, 4-amino-2-chloro-6-(trifluoro-methyl)phenol ot 4-amino-3-(trifluoromethyl)phenol.

In another embodiment, the invention relates to a composition comprising a compound of the formula (V),

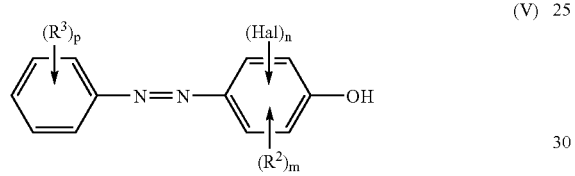

wherein the compound of formula (V) excludes a compound selected from the group consisting of 3,5-difluoro-4-phenylazophenol, 3-fluoro-4-phenylazophenol, 3-fluoro-4-(4'-nitrophenylazo)phenol, 3-fluoro-4-(3'-nitrophenylazo)phenol, 3-fluoro4-(4'-thiocyanatophenylazo)phenol, 3-fluoro-4-(4'-sulphophenylazo)phenol, ethyl 4-(2'-fluoro-4'-hydroxyphenyl-azo)benzoate, 2-fluoro-4-(4'-fluorophenylazo)phenol, 2-fluoro-4-(3'-fluorophenylazo)phenol, 2-fluoro4-(4'-sulphophenylazo)phenol, ethyl 4-(3'-fluoro-4'-hydroxyphenylazo)benzoate, 2,3-difluoro-4-(4'-iodophenylazo)phenol, 2,3-difluoro-4-(4'-sulphophenylazo)phenol and 2,6-difluoro-4-(2'-bromophenylazo)phenol, 3-(trifluoromethyl)-4-(phenylazo)phenol and 3-(trifluoromethyl)-4-(4'-sodium sulphonate phenylazo)phenol, and combinations thereof.

The invention also relates to methods for using the above-mentioned compounds.

These and other features, aspects, and advantages of the present invention will become better understood with reference to the following description and appended claims.

DESCRIPTION

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed in this patent application. Because these ranges are continuous, they include every value between the minimum and maximum values. Unless expressly indicated otherwise, the various numerical ranges specified in this application are approximations.

A process has now been found for preparing compounds of the formula (I)

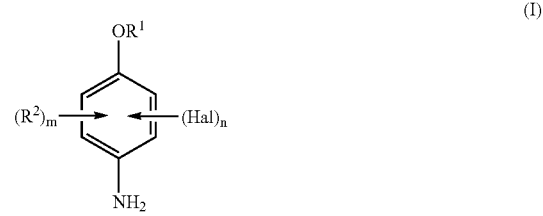

in which
m is 0, 1, 2 or 3 and
n is 1, 2, 3 or 4,
where the sum of
m+n is a maximum of 4, and
$R^1$ is hydrogen, $C_1$-$C_{12}$-alkyl or $C_5$-$C_{15}$-arylalkyl and
$R^2$ is in each case independently $C_1$-$C_{12}$-fluoroalkyl, $C_1$-$C_{12}$-fluoroalkylthio or $C_1$-$C_{12}$-fluoroalkoxy and
Hal is in each case independently bromine, chlorine or fluorine, characterized in that in a step A1),
compounds of the formula (II)

in which
p is 0, 1, 2 or 3 and
$R^3$ is in each case independently fluorine, chlorine, bromine, iodine, cyano, thiocyanato, hydroxysulphonyl or alkali metal salts thereof, nitro, $C_1$-$C_{12}$-alkyl, $C_1$-$C_{12}$-fluoroalkyl, $C_1$-$C_{12}$-fluoroalkyoxy, $C_1$-$C_{12}$-fluoroalkylthio, $C_1$-$C_{12}$-alkoxy, $C_1$-$C_{12}$-alkoxycarbonyl, di($C_1$-$C_{12}$-alkyl)amino, $C_4$-$C_{14}$-aryl or $C_5$-$C_{15}$-arylalkyl
are converted to diazonium salts of the formula (III)

in which $An^-$ is the anion of an acid and
in a step A2),
the diazonium salts of the formula (III) are reacted with compounds of the formula (IV)

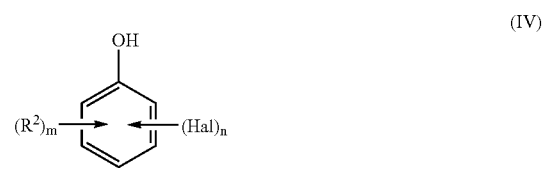

in which
m, n, Hal and $R^2$ are each as defined under the formula (I) in the presence of base to give compounds of the formula (V)

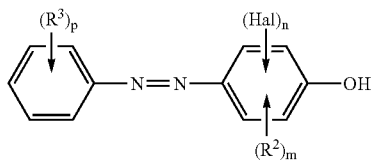

and
in a step B), the compounds of the formula (V) are converted using a reducing agent to the compounds of the formula (I) in which $R^1$ is hydrogen and
optionally, in a step C), these compounds are converted by O-alkylation to compounds of the formula (I) in which $R^1$ is $C_1$-$C_{12}$-alkyl.

This excludes the preparation of 4-amino-3,5-difluorophenol and 4-amino-3-fluorophenol.

Optionally, in a step D),
the compounds of the formula (I) can be converted by reacting with compounds of the formula (VIIa) or (VIIb)

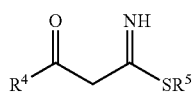

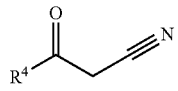

in which
$R^4$ is 2,4-difluorophenyl, 4-fluorophenyl, 2,3-difluorophenyl or 4-fluoro-3-chlorophenyl and
$R^5$ is optionally mono- or poly-chlorine- or -fluorine-substituted phenyl to compounds of the formula (VII)

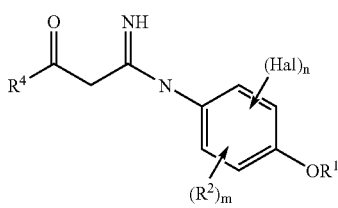

in which
$R^1$, $R^2$, $R^4$, Hal, n and m are each as defined above. Step D) may be carried out in a manner known per se, for example similar to that described in U.S. Pat. No. 4,851,535.

Optionally, in a step E),
the compounds of the formula (VII) can be converted by reacting with compounds of the formula (IX)

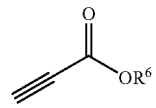

in which
$R^6$ is $C_1$-$C_{12}$-alkyl, $C_5$-$C_{15}$-arylalkyl or $C_4$-$C_{14}$-aryl to compounds of the formula (X)

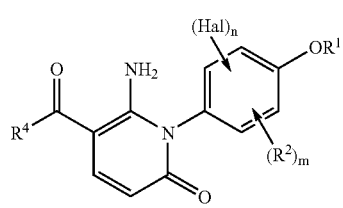

in which
$R^1$, $R^2$, $R^4$, $R^6$, Hal, n and m are each as defined above.

The reaction of the compounds of the formula (VII) with compounds of the formula (IX) to give compounds of the formula (X) may be effected, for example, by heating the two reactants in an organic solvent, preferably an aliphatic alcohol, for example methanol.

The compounds mentioned as exceptions for steps A) to C) are excluded in the same manner for steps D) and E).

In the context of the invention, all radical definitions, parameters and illustrations above and listed herein below, in general or specified within areas of preference, i.e. the particular areas and areas of preference, may be combined as desired.

The term "alkyl" and "alkoxy" are in each case independently a straight-chain, cyclic, branched or unbranched alkyl and alkoxy radical respectively. The same applies to the nonaromatic moiety of an arylalkyl radical.

$C_1$-$C_4$-Alkyl is, for example, methyl, ethyl, n-propyl, isopropyl, n-butyl, sec-butyl and tert-butyl, and $C_1$-$C_{12}$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, n-heptyl, n-octyl, n-nonyl, n-decyl and n-dodecyl.

The term "fluoroalkyl," "fluoroalkoxy" and "fluoroalkylthio" are in each case independently a straight-chain, cyclic, branched or unbranched alkyl, alkoxy and alkylthio radical respectively, each of which is singly, multiply or fully substituted by fluorine atoms.

For example, $C_1$-$C_{12}$-fluoroalkyl is trifluoromethyl, 2,2,2-trifluoroethyl, pentafluoroethyl, nonafluorobutyl, heptafluoroisopropyl, perfluorooctyl and perfluorododecyl.

For example, $C_1$-$C_{12}$-fluoroalkoxy is trifluoromethoxy, 2,2,2-tri-fluoroethoxy, pentafluoroethoxy, nonafluorobutoxy, heptafluoroisopropoxy, perfluorooctoxy and perfluorododecoxy.

For example, $C_1$-$C_{12}$-fluoroalkylthio is trifluoromethylthio, 2,2,2-tri-fluoroethylthio, pentafluoroethylthio, nonafluorobutylthio, heptafluoroisopropylthio, perfluorooctylthio and perfluorododecylthio.

"Aryl" is in each case independently a heteroaromatic radical having 5 to 14 skeleton carbon atoms of which nil, one, two or three skeleton carbon atoms per cycle, but at least one skeleton carbon atom in the entire molecule, may be substituted by heteroatoms selected from the group of nitrogen, sulphur and oxygen, and is preferably a carbocyclic aromatic radical having 6 to 14 skeleton carbon atoms.

In addition, the carbocyclic aromatic radical or heteroaromatic radical may be substituted by up to five identical or different substituents per cycle which are selected from the group of fluorine, cyano, nitro, $C_1$-$C_{12}$-alkyl, $C_1$-$C_{12}$-fluoroalkyl, $C_1$-$C_{12}$-fluoroalkoxy, $C_1$-$C_{12}$-fluoroalkylthio, $C_1$-$C_{12}$-alkoxy, di($C_1$-$C_{12}$-alkyl)amino.

"Arylalkyl" is in each case independently a straight-chain, cyclic, branched or unbranched alkyl radical as defined above, each of which may be singly, multiply or fully substituted by aryl radicals as defined above.

The preferred substitution patterns are defined herein below:

n is preferably 1 or 2,
m is preferably 0 or 1,
$R^1$ is preferably hydrogen or methyl, more preferably hydrogen,
$R^2$ is preferably trifluoromethyl, trifluoromethoxy and trifluoromethylthio,
Hal is preferably bromine, chlorine or fluorine, and at least one Hal radical is more preferably fluorine.
In compounds of the formula (II), p is preferably 0.

The process according to the invention is especially suitable for preparing 4-amino-2,3-difluorophenol, 4-amino-2,5-difluorophenol, 4-amino-2,6-difluorophenol, 4-amino-2-fluorophenol, 4-amino-3-chloro-5-fluorophenol, 4-amino-3-chloro-2-fluorophenol, 4-amino-5-chloro-2-fluorophenol, 4-amino-3-bromo-5-fluorophenol, 4-amino-2-(trifluoromethoxy)phenol and 4-amino-3-(trifluoromethoxy)phenol.

Many of the compounds of the formula (I) are novel and likewise encompassed by the invention, although the following are excluded: 4-amino-3,5-difluorophenol, 4-amino-2,5-difluorophenol, 4-amino-2,6-difluorophenol, 4-amino-2-chloro-6-fluorophenol, 4-amino-2-chloro-3-fluorophenol, 4-amino-2-chloro-5-fluorophenol, 4-amino-2-bromo-5-fluoro-phenol, 4-amino-2-fluorophenol, 4-amino-3-fluorophenol, 4-amino-2-(trifluoromethyl)phenol, 4-amino-5-chloro-2-(trifluoromethyl)phenol, 4-amino-2-chloro-6-(trifluoromethyl)phenol and 4-amino-3-(trifluoromethyl)phenol.

Particularly preferred individual compounds of the formula (I) include: 4-amino-2,3-difluorophenol, 4-amino-3-chloro-5-fluorophenol, 4-amino-3-chloro-2-fluorophenol, 4-amino-5-chloro-2-fluorophenol, 4-amino-3-bromo-5-fluorophenol, 4-amino-2-(trifluoromethoxy)phenol and 4-amino-3-(trifluoromethoxy)phenol.

In step A1), the compounds of the formula (III) can be prepared from compounds of the formula (II) in a manner known per se. Advantageously, the compounds of the formula (II) are reacted with a nitrite source in the presence of water and acid.

The acids used may be, for example, mineral acids such as hydrochloric acid, hydrobromic acid, sulphuric acid or tetrafluoroboric acid, or else organic sulphonic acids.

The nitrite source used may be, for example, the alkali metal nitrites, especially sodium nitrite or potassium nitrite, and also organic nitrites, especially tert-butyl nitrite or methyl nitrite. Preference is given to alkali metal nitrites which are preferably used dissolved in water.

The molar ratio of protons of the acid used to compounds of the formula (II) may be, for example, 1 to 15, preferably 2 to 10 and more preferably 2.5 to 6.5.

The molar ratio of compounds of the formula (II) to the nitrite source may be, for example, 0.8 to 4, preferably 1.0 to 2.5 and more preferably 1.05 to 1.5.

The reaction temperature in step A1) may be, for example, −20° C. to 40° C., preferably −10° C. to 20° C. and more preferably −5° C. to 10° C.; the reaction pressure may be, for example, 0.5 to 100 bar, preferably ambient pressure; the reaction time may be 10 min to 5 hours, preferably 1 hour to 3 hours.

To convert the compounds of the formula (II), the procedure is, for example, to initially charge the compounds of the formula (II) in water and acid and subsequently add an aqueous solution of the alkali metal nitrite. On completion of the reaction time, an excess of alkali metal nitrite may be destroyed by adding a primary amino compound, for example urea or amidosulphuric acid.

The starting compounds of the formula (II) required for step A1) are known from the literature or can be synthesized in a similar manner to the literature.

In step A2), the compounds of the formula (III) obtained in step A1) are reacted with compounds of the formula (IV) in the presence of base to give compounds of the formula (V).

Suitable bases are in principle all bases which are more basic than the compounds of the formula (IV), preferably by at least 2 pK units.

Preference is given to using alkali metal or alkaline earth metal hydroxides, carbonates and hydrogen carbonates, of which alkali metal hydroxides, such as sodium hydroxide in particular, are preferred.

The base may either be initially charged or added in the course of the reaction in such a way that the reaction medium remains alkaline.

The molar ratio of compounds of the formula (III) to compounds of the formula (IV) may be, for example, 0.3 to 5, preferably 0.5 to 2 and more preferably 0.6 to 0.9.

The molar ratio of compounds of the formula (III) to base may be, for example, 1 to 15, preferably 3 to 10 and more preferably 4 to 7.

The reaction temperature in step A2) may be, for example, −20° C. to 50° C., preferably 0° to 40° C. and more preferably 5° to 30° C., the reaction pressure, for example, 0.5 to 100 bar, preferably ambient pressure. In addition, the reaction time may be, for example, 10 min to 15 hours, preferably 3 to 5 hours.

The workup of the compounds of the formula (V) may be effected in a manner known per se by extraction and subsequent distillation, or, in the case of compounds of the formula (V) which are solid at 30° C., by filtration and crystallization.

The compounds of the formula (V) are likewise encompassed by the invention as important intermediates, although the following are excluded: 3,5-difluoro-4-phenylazophenol, 3-fluoro4-phenylazophenol, 3-fluoro-4-(4'-nitrophenylazo)phenol, 3-fluoro-4-(3'-nitrophenylazo)phenol, 3-fluoro-4-(4'-thiocyanatophenylazo)phenol, 3-fluoro4-(4'-sulphophenyl-azo)phenol, ethyl 4-(2'-fluoro-4'-hydroxyphenylazo)benzoate, 2-fluoro-4-(4'-fluorophenylazo)phenol, 2-fluoro-4-(3'-fluorophenylazo)phenol, 2-fluoro-4-(4'-sulphophenylazo)phenol, ethyl 4-(3'-fluoro-4'-hydroxy-phenylazo)benzoate, 2,3-difluoro-4-(4'-iodophenylazo)phenol, 2,3-difluoro-4-(4'-sulphophenylazo)phenol and 2,6-difluoro-4-(2'-bromophenyl-azo)phenol, 3-(trifluoromethyl)-4-(phenylazo)phenol and 3-(trifluoro-methyl)-4-(4'-sodium sulphonate phenylazo)phenol.

The compounds of the formula (IV) are known from the literature or can be synthesized in a similar manner to the literature.

In step B), compounds of the formula (V) are converted by reduction to compounds of the formula (I).

The reduction may be effected, for example, by reducing agents such as sodium bisulphite, titanium(III) chloride or tin and hydrochloric acid. More advantageously, the reduction is carried out in the presence of hydrogen and catalyst.

Preferred catalysts are, for example, metals or metal compounds, especially salts or complexes of nickel, palladium, platinum, cobalt, rhodium, iridium and ruthenium, and preference is given to metals such as nickel or palladium. Metals are preferably used in finely divided form, for example as Raney metal, or applied to a support material.

Particular preference is given to carrying out the reduction with hydrogen and palladium on carbon.

The reduction in step B) may be carried out, for example, at a reaction temperature of 0° C. to 200° C., preferably at 10° C. to 80° C. and more preferably at 20° C. to 40° C.

The partial hydrogen pressure in the reduction may be, for example, 0.1 to 180 bar, preferably 0.5 to 50 bar and more preferably 1 to 3 bar.

Optionally and with preference, the reduction may be carried out in the presence of solvents, as long as they are substantially inert under the reaction conditions selected.

Suitable solvents are, for example, aliphatic, alicyclic or aromatic, optionally halogenated hydrocarbons, for example benzine, benzene, toluene, xylene, chlorobenzene, dichlorobenzene, petroleum ether, hexane, cyclohexane, dichloromethane, chloroform or carbon tetra-chloride; ethers such as diethyl ether, diisopropyl ether, dioxane, tetra-hydrofuran or ethylene glycol dimethyl ether or ethylene glycol diethyl ether; alcohols, for example methanol, ethanol and isopropanol or mixtures of solvents.

In a particularly preferred embodiment, the reduction is carried out in the presence of palladium on activated carbon and in the presence of methanol or ethanol at a partial hydrogen pressure of 1 to 3 bar.

The reaction time in the reduction may be 10 min to 100 hours, preferably 2 to 20 hours.

The workup of the compounds of the formula (I) in which $R^1$ is hydrogen may be effected in a manner known per se by extraction and subsequent distillation or, in the case of compounds of the formula (I) which are solid at 30° C., by recrystallization.

Optionally, step C), the O-alkylation of compounds of the formula (I) in which $R^1$ is hydrogen, is undertaken.

Preference is given in this case to carrying out the reaction in the presence of an inorganic base.

Suitable inorganic bases are in principle all bases which are more basic than the compounds of the formula (I) in which $R^1$ is hydrogen, preferably by at least 3 pK units.

Preferred inorganic bases are alkali metal or alkaline earth metal carbonates, hydrogencarbonates and hydroxides, and also tetraalkylammonium hydroxides, of which preference is given to alkali metal carbonates and hydroxides.

Suitable alkylating agents are in particular compounds of the formula (VI)

$$R^1\text{-Act} \tag{VI}$$

in which
$R^1$ is $C_1$-$C_{12}$-alkyl, $C_5$-$C_{15}$-arylalkyl and Act is iodine, bromine, chlorine or a sulphonate.

Suitable solvents for carrying out the alkylation are in particular ethers such as methyl tert-butyl ether, dioxane, tetrahydrofuran or ethylene glycol dimethyl ether or ethylene glycol diethyl ether; amides such as N, N-dimethylformamide, N, N-dimethylacetamide, N-methylform-anilide, N-methylpyrrolidone, N-methylcaprolactam or hexamethylphosphoramide; sulphoxides such as dimethyl sulphoxide, sulphones such as tetramethylenesulphone or mixtures of such organic solvents.

The molar ratio of inorganic base to compounds of the formula (I) in which $R^1$ is hydrogen may be, for example, 0.3 to 5, preferably 0.5 to 3 and more preferably 0.9 to 1.3.

The molar ratio of alkylating agents to compounds of the formula (I) in which $R^1$ is hydrogen may be, for example, 0.3 to 5, preferably 0.5 to 3 and more preferably 0.9 to 1.8.

The reaction temperature in step C) may be, for example, −70° C. to 100° C., preferably −20 to 60° C. and more preferably 0 to 40° C.

The reaction time in step C) may be, for example, 10 min to 24 hours, preferably 1 to 8 hours.

In the inventive manner, the compounds of the formula (I), (VIII) and (X) are obtained in good yields starting from readily available reactants. The compounds of the formula (I), (VIII) and (X), and also the compounds of the formula (V), are especially suitable for use in a process for preparing active ingredients in pharmaceuticals and agrochemicals, or intermediates thereof.

Preferred active ingredients of pharmaceuticals are those which are used to treat chronic bronchitis, and preference is given to those which are described in WO 03/08413 and PCT 03/02154.

The invention is further illustrated but is not intended to be limited by the following examples in which all parts and percentages are by weight unless otherwise specified.

EXAMPLES

Example 1

Preparation of 3,5-difluoro-4-(phenyldiazenyl)phenol

At 0° C., 108.2 g (1.16 mol) of aniline were dissolved with vigorous stirring in 500 g of 27% hydrochloric acid. Afterwards, at 5°-0° C., 95.2 g (1.38 mol) of sodium nitrite (dissolved in 283 ml of water) were added dropwise and the solution was stirred for another 60 minutes on completion of addition. Excess sodium nitrite was destroyed with amidosulphuric acid. In a further flask, 101.2 g (0.77 mol) of 3,5-difluorophenol were dissolved in a solution of 182.8 g (4.57 mol) of sodium hydroxide in 2281 ml of water, and precooled to 5° C. The above freshly prepared diazonium salt solution is added to this solution at such a rate that the internal temperature did not rise above 5° C. During the addition, the pH was monitored regularly. On completion of addition, the mixture was allowed to warm to room temperature, and stirred for a further 60 minutes, and the suspension was then adjusted to pH 4 using 2N HCl. The product was filtered off and washed repeatedly with water. After the drying in a vacuum drying cabinet, 182 g (quantitative yield) of the desired orange-brown azo compound were obtained.

EI-MS: m/z 234 [M]$^+$

Example 2

Preparation of 4-amino-3,5-difluorophenol 20.4 g (0.09 mol) of 3,5-difluoro-4-(phenyldiazenyl)phenol from Example 1 and 0.5 g of Pd/C (10%) were initially charged in 120 ml of methanol. The solution was degassed and aerated with hydrogen. The mixture was stirred at room temperature under a 1 bar hydrogen atmosphere for 16 hours. On completion of hydrogen uptake, the catalyst was filtered off and the filtrate concentrated on a rotary evaporator. The residue was chromatographed on silica gel (n-hexane/ethyl acetate, 3:1). The resulting solid was stirred with n-hexane and dried. 7.6 g (60%) of 4-amino-3,5-difluorophenol were obtained as a yellow-brown solid.

$^1$H NMR (400 MHz, CDCl$_3$): δ=3.40 (s, 2 H, NH$_2$); 4.55 (s, 1 H, OH); 6.39 (m, 2 H, Ar—H) $^{19}$F NMR (376.3 MHz, CDCl$_3$): δ=−130.5 EI-MS: m/z 145 [M]$^+$ m.p.: 150-151° C.

Example 3

Preparation of 2,3-difluoro-4-(phenyidiazenyl)phenol

At 0° C., 27.3 ml (0.3 mol) of aniline were added dropwise with vigorous stirring to 140 ml of HCl (semiconc.). Afterwards, at 5°-0° C., 21.7 g (0.315 mol) of NaNO$_2$ (dissolved in 100 ml of water) were added dropwise and, on completion of addition, the solution was stirred for another 20 minutes.

In a further flask, 39 g (0.3 mol) of 2,3-difluorophenol were dissolved in 300 ml of 2N NaOH and precooled to 0° C. The above freshly prepared diazo solution was added to this solution at such a rate that the internal temperature does not rise above 5° C. During the addition, the pH was monitored regularly and, if necessary, made alkaline again by means of Na$_2$CO$_3$. On completion of addition, the mixture was allowed to warm to room temperature, stirred for a further 30 minutes and then the suspension was adjusted to pH 3-4 using 2N HCl. The product was filtered off and washed repeatedly with water. After the drying in the vacuum drying cabinet, 61 g (87%) of the desired bright yellow azo compound were obtained.

EI-MS: m/z 234 [M]$^+$

Example 4

Preparation of 4-amino-2,3-difluorophenol 61 g (0.26 mol) of 2,3-difluoro-4-(phenyldiazenyl)phenol from Example 3 and 1 g of Pd/C (10%) are initially charged in 800 ml of ethanol. The solution was degassed and aerated with hydrogen. The mixture was stirred at room temperature under a 1 bar hydrogen atmosphere for 18 hours. On completion of hydrogen uptake, the catalyst was filtered off and the filtrate was concentrated on a rotary evaporator, in the course of which the product already crystallized out. The resulting solid was filtered off, washed with a little cold ethanol and dried under high vacuum for 4 hours. 28 g (74%) of the desired compound were obtained as a light brown powder.

$^1$H NMR (400 MHz, DMSO-d$_6$) δ=4.72 (s, 2H, NH$_2$), 6.39 (t, 1H, Ar—H), 6.51 (t, 1H, Ar—H), 9.13 (s, 1H, OH); EI-MS: m/z 145 [M]$^+$

Example 5

Preparation of 2,5-difluoro4-(phenyidiazenyl)phenol

At 0° C., 17.5 ml (0.19 mol) of aniline were added dropwise with vigorous stirring to 185 ml of HCL (semiconc.). Afterwards, at 5°-0° C., 13.9 g (0.2 mol) of NaNO$_2$ (dissolved in 50 ml of water) were added dropwise and, on completion of addition, the solution was stirred for another 20 minutes.

In a further flask, 25 g (0.19 mol) of 2,5-difluorophenol were dissolved in 190 ml of 2N NaOH and precooled to 0° C. The above freshly prepared diazo solution was added to this solution at such a rate that the internal temperature did not rise above 5° C. During the addition, the pH was monitored regularly and, if necessary, made alkaline again by means of Na$_2$CO$_3$. On completion of addition, the mixture was allowed to warm to room temperature, stirred for a further 30 minutes, and the suspension was then adjusted to pH 3-4 using 2N HCl. The product was filtered off and washed repeatedly with water. After drying in a vacuum drying cabinet at 50° C., 42 g (93%) of the desired orange-coloured azo compound were obtained.

EI-MS: m/z 234 [M]$^+$

Example 6

Preparation of 4-amino-2,5-difluorophenol 42 g (0.18 mol) of 2,5-difluoro-4-(phenyidiazenyl)phenol from Example 5 and 1 g of Pd/C (10%) were initially charged in 650 ml of ethanol. The solution was degassed and aerated with hydrogen. The mixture was stirred at room temperature under a 1 bar hydrogen atmosphere for 18 hours. On completion of hydrogen uptake, the catalyst was filtered off and the filtrate distilled under reduced pressure, and dried under high vacuum at 70° C. for 4 hours. The residue (24 g) was recrystallized from ethanol and dried. 15 g (60%) of 4-amino-2,5-difluorophenol are obtained as orange-brown powder.

$^1$H NMR (400 MHz, DMSO-d$_6$) δ=4.68 (s, 2H, NH$_2$), 6.58 (m, 2H, Ar—H), 9.05 (s, 1H, OH); EI-MS: m/z 145 [M]$^+$

Example 7

Preparation of 2-trifluoromethoxy-4(phenyidiazenyl)phenol

At 0° C., 10.23 ml (0.11 mmol) of aniline were added dropwise with vigorous stirring to 50 ml of HCl (semiconc.). Afterwards, at 5°-0° C., 8.1 g (0.117 mol) of NaNO$_2$ (dissolved in 30 ml of water) were added dropwise and, on completion of addition, the solution was stirred for a further 20 minutes.

In a further flask, 20.0 g (0.12 mol) of 2-trifluoromethoxyphenol were dissolved in 140 ml of 2N NaOH and precooled to 0° C. The above freshly prepared diazo solution was added to this solution at such a rate that the internal temperature did not rise above 5° C. During the addition, the pH was monitored regularly and, if necessary, made alkaline again by means of Na$_2$CO$_3$. On completion of addition, the mixture was allowed to warm to room temperature and stirred for a further 30 minutes, and the suspension was then adjusted to pH 34 using 2N HCl. The product was filtered off with suction and washed repeatedly with water. After drying in a vacuum drying cabinet, 26 g (81%) of the desired light brown azo compound were obtained.

Example 8

Preparation of 4-amino-2-trifluoromethoxyphenol 25 g (0.09 mol) of 2-trifluoromethoxy-4-(phenyldiazenyl) phenol from Example 7 and 1 g of Pd/C (10%) were initially charged in 350 ml of ethanol. The solution was degassed and aerated with hydrogen. The mixture was stirred at room temperature under a 1 bar hydrogen atmosphere for 72 hours. On completion of hydrogen uptake, the catalyst was filtered off and the filtrate concentrated on a rotary evaporator, in the course of which the product already crystallizes out. The resulting solid was filtered off with suction, washed with a little cold ethanol and dried under high vacuum for 4 hours. 8.5 g (50%) of the desired compound were obtained as a light brown powder.

$^1$H NMR (400 MHz, DMSO-$d_6$) δ=4.72 (s, 2H, NH$_2$), 6.42 (d, 1H, J=8.6 Hz, Ar—H), 6.5 (s, 1H, Ar—H), 6.72 (d, 1H, J=8.6 Hz, Ar—H), 8.9 (s, 1H, OH); EI-MS: m/z 193 [M]$^+$.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing compounds of formula (VIII)

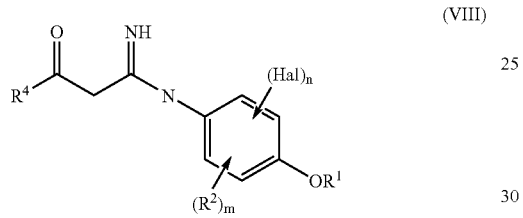

(VIII)

wherein
    m is 0, 1, 2 or 3 and
    n is 1, 2, 3 or 4,
    where the sum of
    m+n is a maximum of 4, and
    R$^1$ is hydrogen, C$_1$-C$_{12}$-alkyl or C$_5$-C$_{15}$-arylalkyl and
    R$^2$ is in each case independently C$_1$-C$_{12}$-fluoroalkyl, C$_1$-C$_{12}$-fluoroalkylthio or C$_1$-C$_{12}$-fluoroalkoxy;
    Hal is in each case independently bromine, chlorine or fluorine; and
    R$^4$ is 2,4-difluorophenyl, 4-fluorophenyl, 2,3-difluorophenyl or 4-fluoro-3-chloro-phenyl
comprising:
(1) preparing compounds of formula (I)

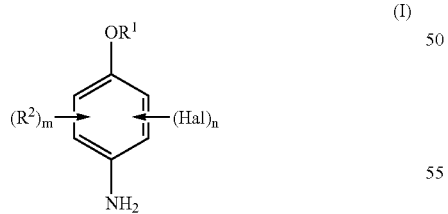

(I)

wherein
    m is 0, 1, 2 or 3 and
    n is 1, 2, 3 or 4,
    m+n is a maximum of 4, and
    R$^1$ is hydrogen, C$_1$-C$_{12}$-alkyl or C$_5$-C$_{15}$-arylalkyl and
    R$^2$ is in each case independently C$_1$-C$_{12}$-fluoroalkyl, C$_1$-C$_{12}$-fluoroalkylthio or C$_1$-C$_{12}$-fluoroalkoxy and
    Hal is each case independently bromine, chlorine or fluorine, by A1) converting a compound of the formula (II)

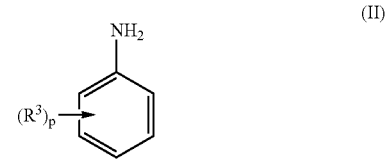

(II)

in which
is 0, 1, 2 or 3 and
R$^3$ is in each case independently fluorine, chlorine, bromine, iodine, cyano, thiocyanato, hydroxysulphonyl or alkali metal salts thereof, nitro, C$_1$-C$_{12}$-alkyl, C$_1$-C$_{12}$-fluoroalkyl, C$_1$-C$_{12}$-fluoroalkyoxy, C$_1$-C$_{12}$-fluoroalkylthio, C$_1$-C$_{12}$-alkoxy, C$_1$-C$_{12}$-alkoxycarbonyl, di(C$_1$-C$_{12}$-alkyl)amino, C$_4$-C$_{14}$-aryl or C$_5$-C$_{15}$-arylalkyl
to a diazonium salt of the formula (III)

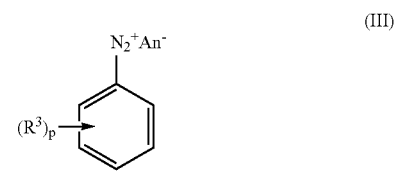

(III)

in which An$^-$ is the anion of an acid and
A2) reacting
the diazonium salt of the formula (III) with compounds of the formula (IV)

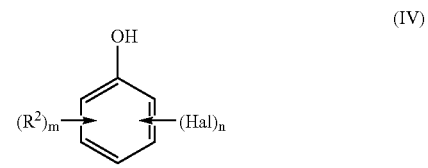

(IV)

in which
m, n, Hal and R$^2$ are each as defined under the formula (I)
in the presence of a base to give compounds of the formula (V)

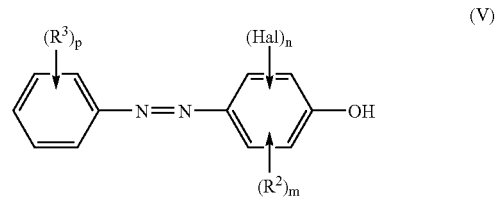

(V)

and

B) converting, a compound of the formula (V) with a reducing agent to the compound of the formula (I), in which R$^1$ is hydrogen, (2) converting at least one compound of formula (I) wherein $R^1$ is hydrogen, by O-alkylation to a compound of formula (I) in which $R^1$ is $C_1$-$C_{12}$-alkyl or $C_5$-$C_{15}$-arylalkyl, and (3) converting at least one compound of the formula (I) of step (2) by reacting with a compound of the formula (VIIa) or (VIIb)

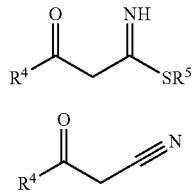

(VIIa)

(VIIb)

wherein
$R^4$ is 2,4-difluorophenyl, 4-fluorophenyl, 2,3-difluorophenyl or 4-fluoro-3-chlorophenyl and
R5 is optionally mono- or poly-chlorine- or -fluorine-substituted phenyl, to the compound of formula (VIII).

2. The process according to claim 1, wherein the compound of formula (I) prepared is selected from the group consisting of 4-amino-2,3-difluorophenol, 4-amino-2,5-difluorophenol, 4-amino-2,6-difluorophenol, 4-amino-2-fluorophenol, 4-amino-3-chloro-5-fluorophenol, 4-amino-3-chloro-2-fluorophenol 4-amino-5-chloro-2-fluorophenol, 4-amino-3-bromo-5-fluorophenol, 4-amino-2-(trifluoromethoxy)phenol and 4-amino-3-(trifluoromethoxy)phenol, and combinations thereof.

3. The process according to claim 1 wherein the process further comprises converting a compound of the formula (VIII) by reacting with compounds of the formula (IX)

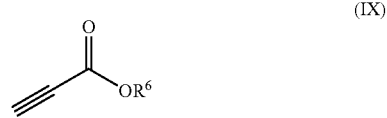

(IX)

wherein
$R^6$ is $C_1$-$C_{12}$-alkyl, $C_5$-$C_{15}$-arylalkyl or $C_4$-$C_{14}$-aryl to compounds of the formula (X)

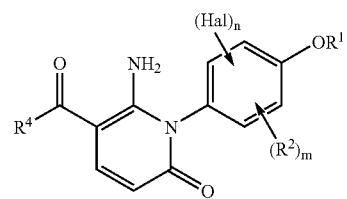

(X)

wherein
m is 0, 1, 2 or 3 and
n is 1, 2, 3 or 4,
where the sum of
m+n is a maximum of 4, and
$R^1$ is hydrogen, $C_1$-$C_{12}$-alkyl or $C_5$-$C_{15}$-arylalkyl and
$R^2$ is in each case independently $C_1$-$C_{12}$-fluoroalkyl, $C_1$-$C_{12}$-fluoroalkylthio or $C_1$-$C_{12}$-fluoroalkoxy and
$R^4$ is 2,4-difluorophenyl, 4-fluorophenyl, 2,3-difluorophenyl or 4-fluoro-3-chlorophenyl, and
Hal is in each case independently bromine, chlorine or fluorine.

* * * * *